(12) United States Patent
Hwang et al.

(10) Patent No.: US 11,511,077 B2
(45) Date of Patent: Nov. 29, 2022

(54) CATHETER FOR SENSING SHAPE AND CONTACT FORCE BY USING FBG OPTICAL FIBER AND CATHETER SYSTEM THEREFOR

(71) Applicants: THE ASAN FOUNDATION, Seoul (KR); UNIVERSITY OF ULSAN FOUNDATION FOR INDUSTRY COOPERATION, Ulsan (KR)

(72) Inventors: Chang Mo Hwang, Seoul (KR); Young Hak Kim, Seoul (KR); Gi Byoung Nam, Seoul (KR); Jae Soon Choi, Seoul (KR); Gi Seok Jeong, Seoul (KR); So Yeon Jin, Cheongju-si (KR)

(73) Assignees: THE ASAN FOUNDATION, Seoul (KR); UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 356 days.

(21) Appl. No.: 16/635,952

(22) PCT Filed: Aug. 1, 2018

(86) PCT No.: PCT/KR2018/008751
§ 371 (c)(1),
(2) Date: Jan. 31, 2020

(87) PCT Pub. No.: WO2019/027254
PCT Pub. Date: Feb. 7, 2019

(65) Prior Publication Data
US 2020/0238051 A1    Jul. 30, 2020

(30) Foreign Application Priority Data
Aug. 2, 2017  (KR) .................. 10-2017-0098010

(51) Int. Cl.
*A61M 25/01* (2006.01)

(52) U.S. Cl.
CPC . *A61M 25/0105* (2013.01); *A61M 2025/0166* (2013.01)

(58) Field of Classification Search
CPC ...... A61M 25/0105; A61M 2025/0166; A61M 2025/0002; A61B 5/282; A61B 5/361;
(Continued)

(56) References Cited

U.S. PATENT DOCUMENTS 7,781,724 B2 * 8/2010 Childers ............ A61B 1/00165
250/227.14
8,567,265 B2 * 10/2013 Aeby ................ A61M 25/0074
606/1
(Continued)

FOREIGN PATENT DOCUMENTS

| CN | 104367324 A | 2/2015 |
| JP | 2014140622 A | 8/2014 |
| KR | 20160120915 A | 10/2016 |
| KR | 20160133048 A | 11/2016 |

OTHER PUBLICATIONS

Polygerinos, Panagiotis et al., "MRI-Compatible Intensity-Modulated Force Sensor for Cardiac Catheterization Procedures" IEEE Transactions on Biomedical Engineering, 2011, vol. 58, No. 3, pp. 721-726.
(Continued)

*Primary Examiner* — Sanjay Cattungal
(74) *Attorney, Agent, or Firm* — Casimir Jones, S.C.; Brian F. Bradley

(57) ABSTRACT

The present invention is advantageous in that the shape of the catheter can be sensed by detecting the position of bending of the catheter body, the direction thereof, the angle thereof, and the curvature thereof through a triplet calculation of information regarding three wavelengths that have undergone a transition along respective FBGs provided on three optical cores.

16 Claims, 10 Drawing Sheets

(58) Field of Classification Search
CPC .... A61B 2034/2051; A61B 2034/2053; A61B 2034/2061; A61B 2034/2072; A61B 5/061; A61B 5/6852; A61B 5/0084; A61B 2505/05; A61B 2562/0233; A61B 34/20; A61B 34/30; A61B 2017/00778; A61B 2034/2055; A61B 2034/301
See application file for complete search history.

(56) References Cited

U.S. PATENT DOCUMENTS

| | | | | |
|---|---|---|---|---|
| 8,900,131 | B2* | 12/2014 | Chopra | A61B 1/009 600/407 |
| 2016/0279388 | A1* | 9/2016 | Barrish | A61M 25/1034 |
| 2018/0071492 | A1* | 3/2018 | Laby | A61M 25/0155 |
| 2021/0138198 | A1* | 5/2021 | Leo | A61M 25/0158 |

OTHER PUBLICATIONS

St. Jude Medical_TactiCath™ Contact Force Ablation Catheter, Sensor Enabled™, 2018, 32 pages.
Tina Lin et al., THERMOCOOL® SMARTTOUCH® CATHETER—The Evidence So Far for Contact Force Technology and the Role of VisiTag™ Module, Radcliffe Cardiology, Arrhythmia & Electrophysiology Review, 2014, pp. 44-47.
Choi, Jong-Il et al., "NavXTM cardiac mapping system" The Official Journal of Korean Heart Rhythm Society, vol. 14, No. 1, Mar. 2013, pp. 8-13.
Biosense Webster_CARTO® 3 System Fact Sheet, 2014, 3 pages.
Gepsi Ein, Lior et al., "A Novel Method for Nonfluoroscopic Catheter-Based Electroanatomical Mapping of the Heart" American Heart Association Journals, Mar. 1997, 25 pages.
International Search Report, International Patent Application No. PCT/KR2018/008751, dated Jan. 16, 2019, 2 pages.

* cited by examiner

CATHETER FOR SENSING SHAPE AND CONTACT FORCE BY USING FBG OPTICAL FIBER AND CATHETER SYSTEM THEREFOR

TECHNICAL FIELD

Example embodiments relate to a catheter for sensing a shape using a Fiber Bragg Grating (FBG) optical fiber, and a catheter system including the same. More specifically, example embodiments relate to a catheter and a catheter system configured for calculating a shape of deformation of a catheter body and a direction and a magnitude of a contact force applied to a front end of the catheter using light wavelength information and thus suitable for a cardiovascular interventional surgical procedure.

BACKGROUND ART

In general, a catheter is a medical device used to insert a tube into a patient's body to treat an affected area using a high frequency, or to inject a medical substance into the body and to discharge a body fluid from the body to an outside thereof.

In performing a surgical procedure using the catheter, when a tip as a front end of the catheter exerts an excessive pressure on the affected portion of the patient, the affected portion may be damaged. On the contrary, when the front end of the catheter contacts the affected area while too little pressure is applied thereto, the affected portion may not be treated properly. Therefore, the pressure applied to the affected portion needs to be precisely measured based on a location and a type of the surgical procedure.

In one example, a treatment and surgical procedure via inducing the catheter a target affected portion using an imaging device is referred to as an interventional surgical procedure. The interventional surgical procedure is characterized by a minimal invasion, which increases safety of the surgical procedure, results in excellent patient prognosis, minimizes a pain and a scar, and thus leads to a high patient satisfaction and has an increased scope of applications thereof. However, the interventional surgical procedure requires precise manipulation of a medical practitioner during the surgical procedure. Thus, success or failure of the procedure depends on experience and ability of the medical practitioner. Further, in treatment of a sensitive area such as a cardiovascular vessel depending on a type of the surgical procedure, the medical practitioner may fail to precisely position the catheter, resulting in damage to the vessel. Further, the interventional surgical procedure may cause other complications, radiation exposure, and the like. Thus, a medical device and equipment to enable precise and accurate surgical procedures in a short time is urgently needed. In other words, in order to minimize the complications of the patient depending on the experience and ability of the medical practitioner and in order to avoid the continuous radiation exposure of the medical practitioner as a number of patients are treated, configuring a control system to remotely perform the interventional surgical procedure is recognized as a major technical issue.

In order to configure the remote control system for a cardiovascular intervention procedure, main hardware components of the system may include a catheter to be guided to a heart for the interventional surgical procedure, a master (haptic master manipulator) to allow the medical practitioner to operate the catheter, and a slave (slave robot) that controls the catheter in conjunction with the manipulation of the master. In this connection, the catheter deliveries a stent or has an electrode for high frequency ablation to perform radiofrequency catheter ablation. As mentioned above, the catheter requires the precise control thereof. When the medical practitioner controls remotely the catheter, functional precisions of sensing information of a contact between a tip of the catheter and a tissue in a body, location information of each of portions of the catheter, electrocardiogram information detected by an electrode sensor included in the catheter will directly affect the success or failure of the surgical procedure.

In the cardiovascular interventional surgical procedure, the catheter enters the heart and an electrode disposed on a surface portion of the catheter contacts the heart's inner wall to map the heart. In the cardiovascular intervention, it is particularly important that a magnitude and direction of a contact force (pressure) onto a front end of the catheter be precisely measured. When RF is applied while the catheter is not in contact with a target tissue during the radiofrequency catheter ablation, a blood around the catheter electrode located inside the atrium is solidified to cause a blood clot, leading to cerebral infarction and major organ embolism. To the contrary, when cautery is executed while the catheter contacts, at an excessive pressure, the inner wall of the heart where the atrial inner wall is constantly contracting and relaxing, this may cause a major medical accident such as a puncture of the inner wall.

As the precise measurement of the pressure applied to the front end of the catheter during mapping or tissue radiofrequency ablation, various types of sensors have been proposed to measure the pressure applied to the tip of the catheter. Conventionally, a force sensor using an electric based pressure sensing element in which an output current varies based on a force applied externally is used. However, in the force sensor using the electric based pressure sensing element, change of the output current may be small when a small external force is applied. Thus, an expensive equipment is further needed to accurately measure change in the current. Further, when the amount of the current is increased by increasing a size of the electric based pressure sensing element, a size of the catheter increases such that the electric based pressure sensing element is not combined with the catheter to be inserted into a blood vessel.

Accordingly, a prior art proposing another solution to measure the pressure applied to the tip of the catheter includes U.S. Pat. No. 8,567,265 disclosing a catheter that senses a force applied to the front end thereof in three axial directions using an optical fiber. FIG. 1 shows the catheter in U.S. Pat. No. 8,567,265. Referring to FIG. 1, the catheter in U.S. Pat. No. 8,567,265 uses not the conventional electric based pressure sensing element but the optical fiber to calculate a flexure and a contact pressure via analysis of Fabry-Perot interferometer resulting from reflection of light occurring when the front end of the catheter is flexed. The catheter in U.S. Pat. No. 8,567,265 as shown in FIG. 1 has a sensing assembly 92 having a structural member 102 having three level gaps 921. In this connection, the structural member 102 has threes slit-shaped gaps 921 having different levels, each gap being defined, by 120°, in an outer circumferential surface thereof. In this connection, three optical fibers 104 are arranged in three positions spaced from each other by 120 degrees so that an output end of an optical core of each optical fiber is located in each gap 921. The three-level gaps 921 forms a spring-like segmented structure. When an external force F is applied to the front end of the catheter in a certain direction, a spacing of each gap 921 at each position may vary. Accordingly, a multi-interference phenomenon of the light thus reflected and received by the optical fiber 104 is analyzed to detect the magnitude and direction of the contact force.

FIG. 2 illustrates a principle of a catheter to which the catheter configuration disclosed in FIG. 1 of U.S. Pat. No. 8,567,265 and is an excerpt from a TactiCath™ product description from St. Jude Medical company. The Fabry-Perot interferometer is generally composed by inserting one resonant layer (gap cavity) between two high reflectivity mirrors. A fundamental principle of the Fabry-Perot interferometer is that when light of multi-wavelengths λ1, λ2, and λ3 transmitted through an optical fiber is incident on a filter, multiple interferences are caused in the resonant layer, thereby transmitting light of only a certain wavelength and reflecting light of other wavelengths, thereby to select desired data. Referring to FIG. 2, the gap 921 of the structural member 102 is shown as a Fabry-Perot cavity. It may be understood that the direction and magnitude of the external force are calculated using wavelength information of the light subjected to multi interferences through the three gaps 921 under the Fabry-Perot interferometer.

Other products to which a configuration of the catheter for sensing the pressure applied to the front end as shown in FIG. 1 and FIG. 2 include ThermoCool SmartTouch catheter from Johnson & Johnson Medical's Biosense Webster. The Thermocool SmartTouch catheter accurately transmits a strength and direction of a contact force of the catheter and improves safety and is approved by USFDA and is available in Korea.

As such, an approach for measuring the pressure applied to the tip of the catheter is being developed from a catheter employing the electrical based pressure sensing element to a catheter employing the optical fiber having excellent safety and excellent sensitivity and having a small diameter to allow the optical fiber to be easily assembled with the catheter.

However, the conventional catheter as described with reference to FIG. 1 and FIG. 2 requires the structural member 102 in addition to the optical fiber as the sensing assembly 92. In this connection, in the structural member 102, the slit shaped gaps 921 should be arranged at 120° spacing and be formed to have different levels. That is, the structural member 102 should have at least three gaps 921 equally spaced from each other and arranged in a longitudinal direction of the structural member. Therefore, in the conventional catheter, a length of the structural member 102 may occupy most of a length of the front end of the catheter. Thus, there is a limit in measuring precise displacement of the front end of the catheter. Further, analyzing the wavelength information of light using the multiple interference phenomenon such as the Fabry-Perot interferometer causes a problem that a system design is complicated and a manufacturing cost increases accordingly.

Further, in the cardiovascular interventional surgical procedure, the mapping of the heart and a location of the catheter currently inserted into the mapped heart should be accurately identified. In this regard, conventionally, the catheter position in the heart was identified in real time using an electro-anatomical mapping (EAM) technique. The electro-anatomical mapping technique refers to a non-contact mapping system that constructs the catheter position in a three dimensional manner via a patch on a body surface that induces a transthoracic electric field using a multi-electrode array.

FIG. 3 illustrates a principle of Ensite NavX™ product from St. Jude Medical to which the electro-anatomical mapping is applied and is an excerpt from a "three-dimensional mapping system" document published in the International Journal of Arrhythmia. Referring to FIG. 3, the Ensite Nav™ is an impedance-based mapping system in that six electrode patches in total are attached: one pair at front and back, one pair at left, and right, and one pair at lower and upper on the patient's surface; when a current signal of about 8 KHz is emitted from each of the six electrodes, the transthoracic electric field is generated to form a voltage gradient through tissues in the heart along each axis; this voltage is measured at the catheter's electrode in the heart and thus the catheter position is determined.

However, the non-patent literature pointed out that the impedance-based cardiac mapping method has a natural disadvantage that accuracy of a 3D image is reduced due to deformation of the electric field caused by a technical problem. Therefore, an experience of a person who performs the surgical procedure in a registration process is suggested as an important factor to reduce the error.

In another example, a system that detects the location of the catheter using a magnetic field is proposed as a mapping method different from the above-described electro-anatomical mapping method as shown in FIG. 3. FIG. 4A and FIG. 4B illustrate a principle of a CARTO product from Biosense Webster to which the magnetic field mapping is applied and are relevant drawings taken from a literature 'A Novel Method for Nonfluoroscopic Catheter-Based Electro-anatomical Mapping of the Heart'. Referring to FIG. 4A, in the Biosense Webster's CARTO product, a ring-shaped electrode is disposed at a tip of a mapping catheter, and a location sensor is housed inside the catheter. Referring to FIG. 4B, a location pad is composed of three coils C1, C2, and C3, each forming a magnetic field. The location sensor built into the catheter measures a strength of the magnetic field of the location pad. Thus, a distance is calculated based on the strength to map the location of the catheter.

However, the non-patent literature pointed out that the position sensing using the magnetic field has a cost advantage compared to a fluoroscopy based catheter system, but in the position sensing approach using the magnetic field, a system acquiring a precise mapping in real time is not yet optimized. Further, the non-patent literature pointed out that rapid detection of the catheter bending is still a technical challenge, and thus the position sensing approach using the magnetic field is currently used in combination with a traditional mapping guide catheter.

In conclusion, the electro-anatomical mapping technique performs three-dimensional mapping based on the transthoracic electric field and thus has a limitation that anatomical accuracy is reduced due to variation of a reference source or change of the electric field resulting from movement of the heart and breathing of the patient during an actual surgical procedure. Further, it has a limitation that the mapping catheter disallows concurrent mapping based on concurrent contacts of multiple electrodes but allows sequential mapping based on sequential contact of the multiple electrodes. Thus, activation mapping cannot be performed in arrhythmias having unstable beats such as atrial fibrillation. Further, the magnetic field based mapping technique may not obtain deformation information such as the catheter bending in real time, and optimization of the system remains as a challenge. Accordingly, there is a need for another method of mapping that may improve the accuracy of mapping the heart shape and sensing the location of the catheter.

Accordingly, with referring to U.S. Pat. No. 7,781,724, the present applicant has designed a catheter and a catheter system for a cardiovascular interventional surgical procedure for detecting the shape of the catheter itself in real time without formation of an electric or magnetic field to obtain a coordinate value thereof and thus to determine the location of the catheter based on the coordinate value.

U.S. Pat. No. 7,781,724 discloses a technique for detecting, in real-time, a shape of a bending and a position of an optical fiber using three FBG optical fibers. FIG. 5 shows an optical fiber shape sensing device 10 disclosed in U.S. Pat. No. 7,781,724 (hereinafter, "prior patent"). Referring to FIG. 5, the device in the prior patent includes an optical fiber 20 having three or more optical cores 30, 35 and 40, FBG 50 provided in each of the optical cores 30, 35 and 40, a reflectometer 70, and a coupling device 25 for coupling multiple optical fibers 55, 57 and 59. The FBG 50 is a kind of an optical sensor and stands for Fiber Bragg Grating and reflects light of a wavelength varying in response to temperature or deformation. Each FBG 50 is manufactured to have each unique Bragg wavelength. Each FBG 50 extending in a longitudinal direction of the optical core reflects light of an unique wavelength and shifts the reflected light wavelength according to change in the FBG slit spacing due to temperature or deformation at a corresponding location. Thus, deformation of strain applied to the optical fiber may be detected.

The prior patent according to FIG. 5 detects frequency displacement from the FBG 50 located in the same cross section of the three optical cores 30, 35 and 40 arranged at a 120° spacing. Two-dimensional shape deformation of the optical fibers 55, 57, and 59 may be determined by calculating frequency displacement measured at the two optical cores. The prior patent discloses that three-dimensional shape deformation of the optical fibers 55, 57, and 59 may be determined via calculation of frequency displacement measured at the three optical cores.

The present applicant has confirmed that the three-dimensional shape of the optical fiber may be measured using at least three FBG optical cores and thus has noted that coordinate values of the FBG obtained via the shape sensing of the catheter may act as a problem-solving factor to detect the exact position of the catheter. Accordingly, with reference to the prior patent, the present applicant has been able to devise a catheter that realizes the shape detection of the catheter and the pressure sensing of the front end at the same time and thus is particularly suitable for the cardiovascular interventional surgical procedure.

A related non-patent literature includes "NavX™ cardiac mapping system" (Choi Jong Il), International Journal of Arrhythmia 2013; 14(1): 8-13. and "A Novel Method for Nonfluoroscopic Catheter-Based Electro-anatomical Mapping of the Heart" Lior Gepstein, Mar. 18, 1997.

DETAILED DESCRIPTION OF THE INVENTION

Technical Subject

The present disclosure aims to provide a catheter and a catheter system that may detect the three-dimensional shape of the catheter in real time, and may measure the direction and magnitude of the external force applied to the front end of the catheter.

Further, the present disclosure aims to provide a catheter and a catheter system designed to have an excellent bending range in consideration of a moving range of an inflexible optical fiber.

Further, the present disclosure aims to provide a catheter and a catheter system with improved measurement sensitivity to accurately determine a bending location of the optical fiber in consideration of optical interference of FBG reflective light.

Further, the present disclosure aims to provide a catheter that may measure a magnitude of the external force while identifying three-axis directions of the external force applied to the front end of the catheter based on three light wavelength information.

Further, the present disclosure aims to provide a catheter that may measure external force more precisely because a sensing assembly for sensing the external force may be formed in a micro region at the front end of the catheter.

Solutions

According to an aspect, there is provided an catheter including: a catheter body having first and second regions, wherein one or more channels are formed in the first region, while the second region includes a front end having a tip subjected to an external force and thus bent; an optical fiber inserted into the channel and having a plurality of Fiber Bragg Gratings (FBGs) arranged along a longitudinal direction of the catheter body; and an elastic member to surround the optical fiber and disposed inside the front end, wherein the elastic member is made of a material having a different elastic force from an elastic force of the catheter body to concentrate the external force applied to the tip on the front end, wherein the plurality of FBGs senses a shape of the catheter body based on light wavelength information corresponding to a group of FBGs placed in the first region, and senses the external force applied to the tip based on light wavelength information of a group of FBGs placed in the second region.

Preferably, the optical fiber may have three or more optical cores, wherein the three or more optical cores are arranged around a linear axis of the catheter body in a radius of 0.01 mm to 1.00 mm from the axis.

Preferably, the plurality of FBGs may be arranged in the optical fiber such that spacings between adjacent FBGs vary, wherein the spacings increase toward the front end.

Preferably, the plurality of FBGs may be arranged in the optical fiber such that spacings between adjacent FBGs vary, wherein the spacings decrease toward the front end.

Preferably, the elastic member may be disposed in the second region such that the group of FBGs placed in the second region is located inside the elastic member.

Preferably, the optical fiber may have three or more optical cores, wherein light of the same wavelength band is incident on the three or more optical cores.

Preferably, the optical fiber may have three or more optical cores, wherein light of different wavelength bands are incident on the three or more optical cores.

Preferably, the three or more optical cores may discriminate between shifted wavelength information of light of different wavelength bands passing through the group of FBGs arranged in the first region, and calculate a direction and angle of the bending of the optical fiber based on the discriminated three or more light wavelength information to sense the shape of the catheter body.

Preferably, the optical fiber may have three or more optical cores, wherein light is incident on the three or more optical cores at different timings.

Preferably, the three or more optical cores may discriminate between light information based on the different timings at which the light of the same wavelength band passes through the group of FBGs arranged in the first region, and calculate a direction and angle of the bending of the optical fiber based on the discriminated three or more light wavelength information to sense the shape of the catheter body.

Preferably, when light of the same wavelength band passes through the three or more optical cores in the first region to form different light paths, the three or more optical cores may discriminate between the light information via the respective groups of FBGs disposed inside the optical cores, and calculate a direction and angle of the bending of the optical fiber based on the discriminated light wavelength information to sense the shape of the catheter body.

Preferably, the optical fiber may have three or more optical cores, wherein the three or more optical cores sense a direction and a magnitude of the external force exerted on the tip based on shifted three or more wavelength information of light passing through the group of FBGs placed in the second region.

According to another aspect, there is provided a catheter system including: a catheter including: a catheter body having first and second regions, wherein one or more channels are formed in the first region, while the second region includes a front end having a tip subjected to an external force and thus bent; an optical fiber inserted into the channel and having a plurality of FBGs arranged along a longitudinal direction of the catheter body; and an elastic member to surround the optical fiber and disposed inside the front end, wherein the elastic member is made of a material having a different elastic force from an elastic force of the catheter body to concentrate the external force applied to the tip on the front end; and a light-wavelength analyzer to calculate a shape of the catheter body based on light wavelength information corresponding to a group of FBGs placed in the first region, and to calculate the external force applied to the tip based on light wavelength information of a group of FBGs placed in the second region, wherein the catheter includes an electrode disposed outside of the catheter body to transmit an electrical signal to the analyzer through a wire placed inside the catheter body and to transmit energy input from an outside to a tissue.

Preferably, the optical fiber of the catheter may have three or more optical cores, wherein the light-wavelength analyzer calculates a direction and an angle of the bending of the optical fiber based on wavelength information of three or more light received from the three or more optical cores to sense the shape of the catheter body.

Effects

In accordance with the present disclosure, the triplet calculation of three shifted wavelength information of light through the FBGs provided in each of the three optical cores may allow detecting the location, direction and angle of the bending of the catheter body to achieve the shape sensing of the catheter.

Further, in accordance with the present disclosure, the optical fiber is located in the center corresponding to the axis of the catheter body. In this connection, the three or more optical cores may be arranged around the linear axis in a radius of 0.01 mm to 1.00 mm from the linear axis. This configuration is in contrast to U.S. Pat. No. 8,567,265, in which a plurality of optical cores should be disposed outside of the catheter body. This is a structural design that may improve the bending range of the catheter in consideration of the moving range of the inflexible optical fiber.

Further, in accordance with the present disclosure, the FBGs are arranged so that the spacing between adjacent FGBs arranged along the length direction of each of the optical cores increase in the front end direction. This minimizes the loss of the reflective light due to interference between the light passing through the FBGs to improve a resolution of detecting the bending position.

Further, in accordance with the present disclosure, the region in which the FBG is disposed in each of the optical cores is discriminated. The shifted wavelength corresponding to the group of FBGs in the first region is used for the shape sensing. The shifted wavelength corresponding to the group of FBGs in the second region is used for the pressure sensing. Thus, the sensing assembly is configured to detect the shape and pressure of the catheter using only three or more optical cores. Thus, the sensing assembly is particularly suitable as sensing means of a mapping catheter that must be implemented to have a small radius.

BEST MODE FOR CARRYING OUT THE INVENTION

Figure 1:
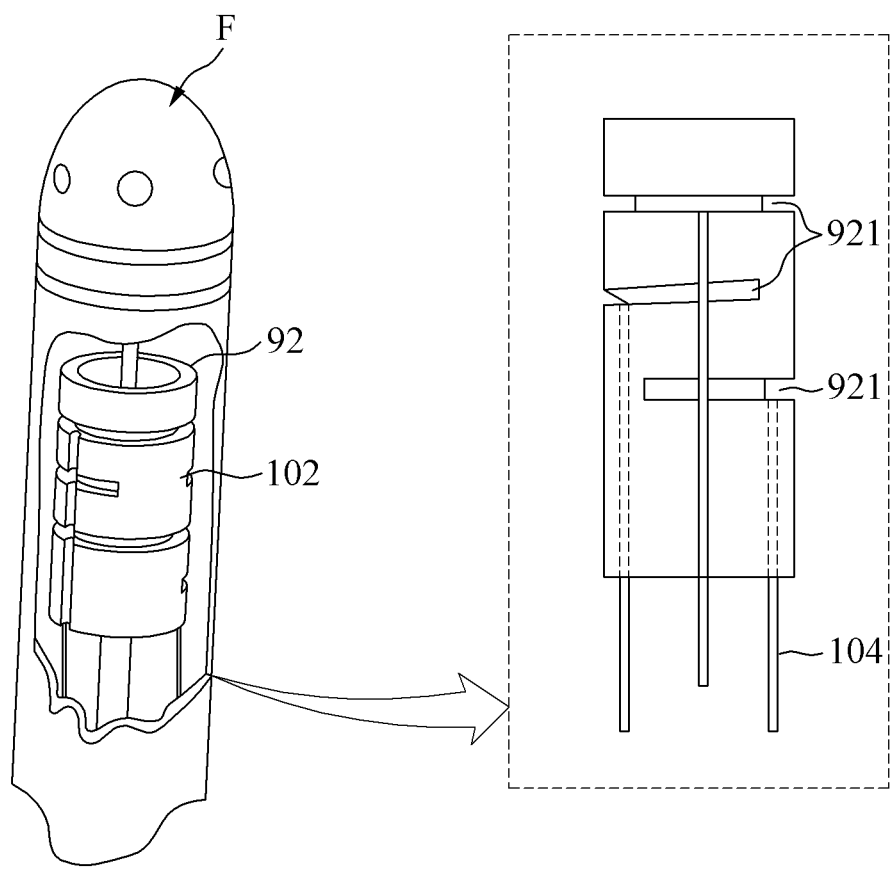
FIG. 1 illustrates a conventional catheter for sensing a pressure using an optical fiber.
Figure 2:
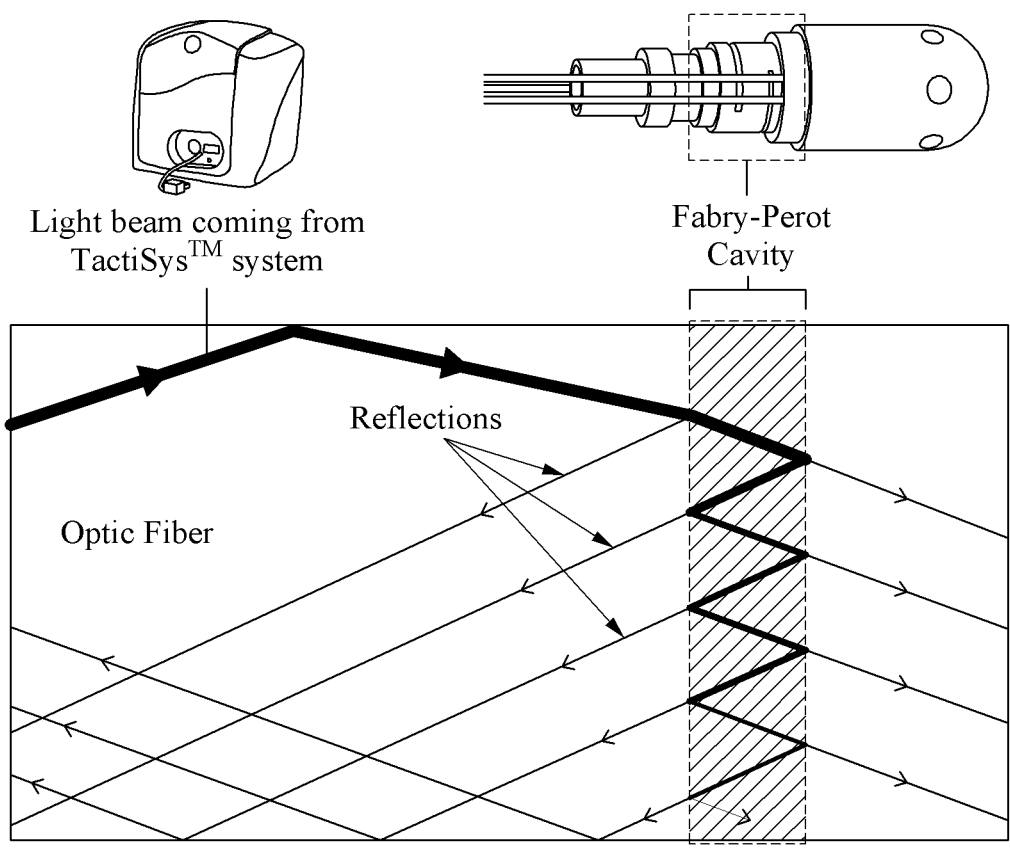
FIG. 2 illustrates a sensing principle of a catheter product for sensing a pressure to which the conventional catheter for sensing a pressure of FIG. 1 is applied.
Figure 3:
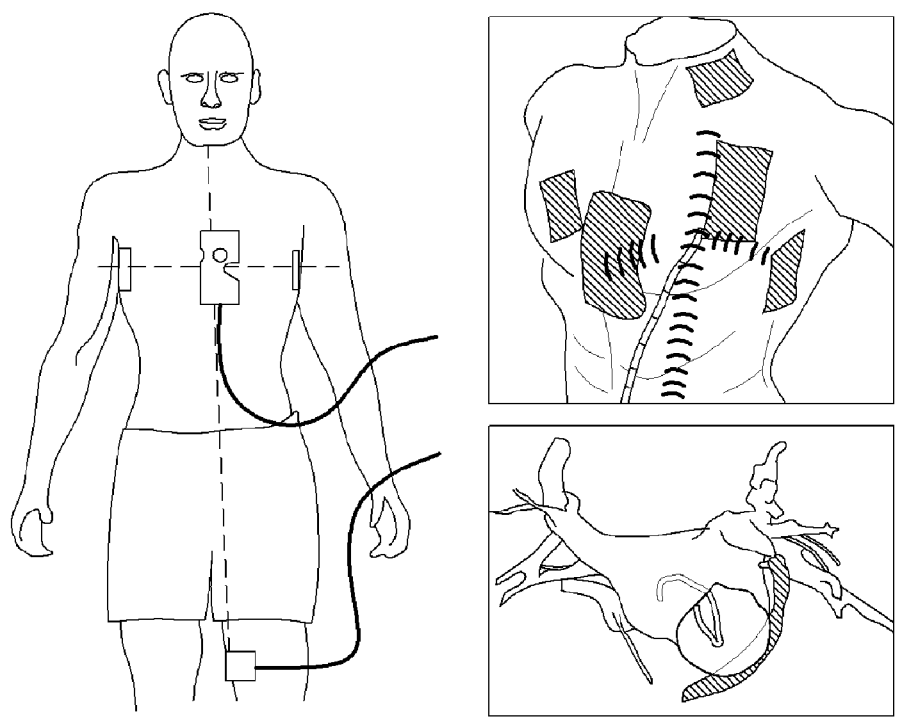
FIG. 3 shows a conventional catheter system according to the electro-anatomical mapping technique.

Hereinafter, the present disclosure will be described in detail with reference to the accompanying drawings. However, the present disclosure is not restricted or limited to the exemplary embodiments. Like reference numerals in the drawings denote members that perform substantially the same function.

The purpose and effect of the present disclosure may be naturally understood or clarified from the following description. The following description does not limit the purpose and effect of the present disclosure. Further, in describing the present disclosure, when it is determined that detailed descriptions of a well-known component related to the present disclosure may unnecessarily obscure gist of the present disclosure, the detailed description thereof will be omitted.

Figure 6:
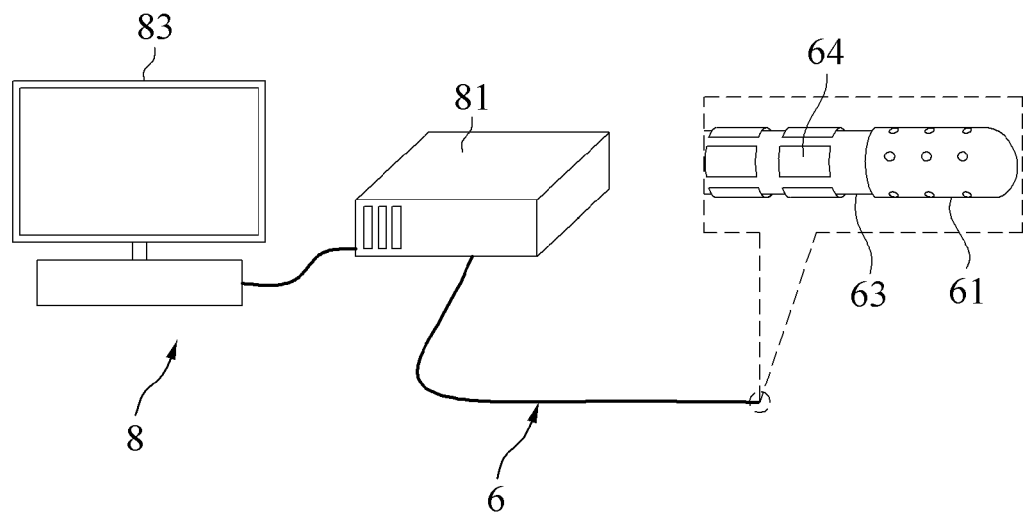
FIG. 6 and FIG. 7 illustrate a catheter system according to an embodiment of the present disclosure.
Figure 7:
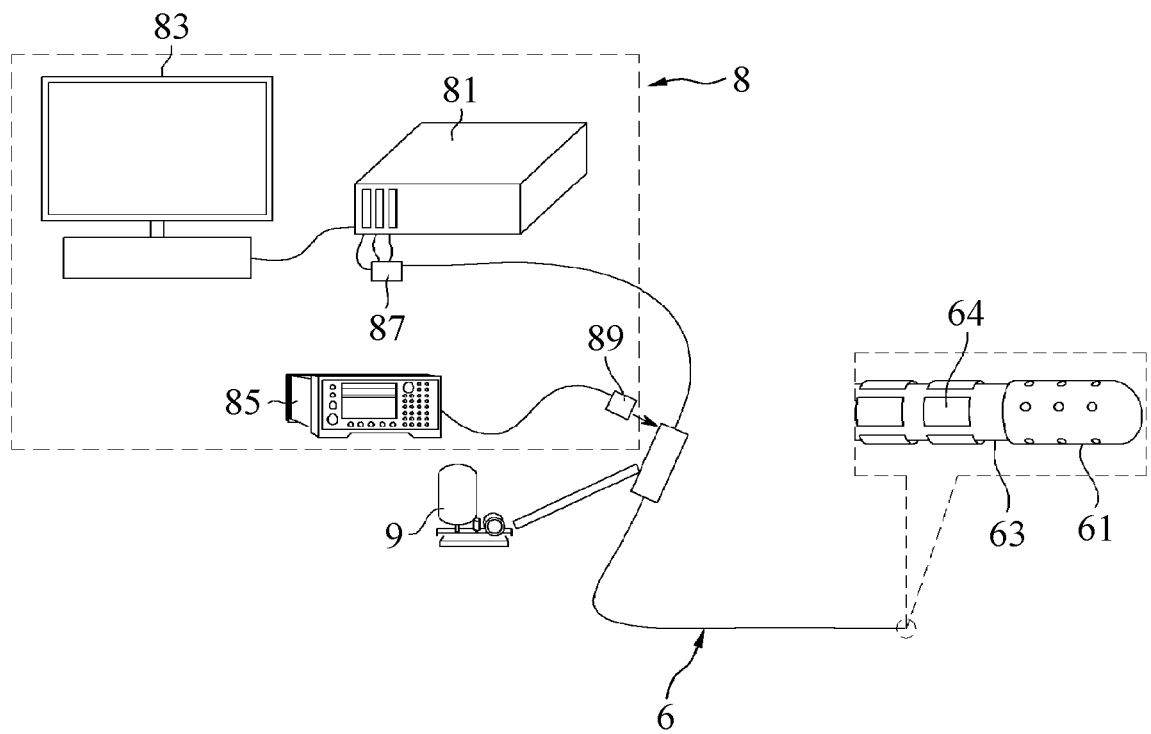

FIG. 6 and FIG. 7 illustrate a catheter system 1 according to an embodiment of the present disclosure. Referring to FIG. 6, the catheter system 1 according to the present embodiment may include a catheter 6, a light-wavelength analyzer 8, and a coolant pump 9. The catheter system 1 according to the present embodiment is configured to measure a magnitude and direction of an external force applied to a tip 61 of the catheter 6 to obtain three-dimensional pressure information of the tip 61 in contact with an inner wall of a heart. In the catheter system 1 according to the present embodiment, an optical fiber 65 is implemented as a sensing assembly for measuring the pressure of the tip 61.

Further, the sensing assembly composed of the optical fiber 65 may determine a magnitude and a direction of the external force applied to the tip 61 as well as may sense a shape of a catheter body 63 based on a location, a degree and a direction of bending in which the catheter body 63 is bent. In this case, the pressure measurement of tip 61 and the shape sensing of the catheter 6 are calculated by using light wavelength information resulting from FBGs 6511 and 6513 provided in the optical fiber 65. The light wavelength information is classified into information corresponding to a group of FBGs 6511 for the shape sensing of the catheter body 63 and information corresponding to a group of FBGs 6513 for measuring the pressure of the tip 61. The measuring principle will be described later with reference to FIGS. 7 to 9.

The catheter system 1 according to the present embodiment may include the light-wavelength analyzer 8 and the catheter 6. The light-wavelength analyzer 8 may include a processor to calculate a plurality of light wavelength information received from the optical fiber 65 to calculate the magnitude and direction of the external force applied to the tip 61 and the shape of the catheter body 63, and a display 83 which visually presents the calculated result. Hereinafter, a detailed configuration of the catheter 6 according to the present embodiment will be described in detail.

The catheter 6 may include the catheter body 63, the optical fiber 65, the tip 61, an electrode 64, and an elastic member 67.

The tip 61 may be implemented in a form of an ablation electrode for radiofrequency catheter ablation. The tip 61 may be electrically connected with an electrode wire 33 and may be heated with externally applied power to remove cardiac muscular tissue. In another embodiment, the tip 61 may be implemented as an electrical sensor element capable of measuring a bio-signal such as ECG. The tip 61 is coupled to a front end of the catheter body 63. One or more driving wires 615 are connected to the tip 61, such that the catheter 6 may be steered as a direction of the front end is controlled via inflow and outflow of the driving wires 615. Water supply holes 613 may be defined in an outer surface of the tip 61. Coolant delivered to an irrigation tube 31 may be discharged through the water supply holes 613.

In this embodiment, referring to the enlarged view of FIG. 6, the catheter 6 may be configured such that a plurality of electrodes 64 is exposed to a surface of the catheter body 63 in addition to an electrode provided at the tip 61. In this case, the plurality of electrodes 64 provided on the surface of the catheter body 63 may act as an ablation electrode to execute cautery of cardiac muscular tissue. Although not shown in the drawing, each of the electrodes 64 may be connected to the driving wire 615 and the electrode wire 33 so that a region of the catheter body 63 in which the electrodes 64 are located may be bent. Accordingly, the catheter body 63 may form a loop at the front end. The loop formed by the body 63 rather than the tip 61 is in contact with a target point, thereby allowing the plurality of the electrode 64 to cauterize a large area.

In the present embodiment, the electrodes 64 may be provided in a form of four to six divided segments on a circumferential surface of the catheter body 63. During ablation, one side of a circumference of the loop of the catheter body 63 is in contact with the target point. Accordingly, the electrodes 64 are arranged along the circumferential surface of the catheter body 63. When high frequency is applied to the electrode, blood clot may occur on the other and non-contacting side, thereby causing side effects. Thus, the catheter 6 may be implemented such that the electrodes 64 may be provided on the catheter body 63 in the form of divided segments as shown in FIG. 6 and the high frequency may be applied only to the segmented electrode 64 in contact with the target point.

Alternatively, the electrodes 64 may be provided outside the catheter body 63 to transmit electrical signals to the analyzer through wires disposed inside the catheter body 63 or to transmit energy from the outside to the tissue.

The catheter body 63 enters the heart and guides, to a target site, a treatment instrument such as the electrode which must be inserted to remove the cardiac muscular tissue. In treatment of tachyarrhythmias, such as paroxysmal atrophy, atrial tachycardia, and paroxysmal ventricular tachycardia, the heated electrode comes into contact with the tissue to remove the cardiac muscular tissue. The electrode performs ablation for about 60 seconds at about 50 to 60° C. As such, a catheter in which the electrode reaches the arrhythmia site and removes the cardiac muscular tissue to treat the arrhythmia may be classified as an ablation catheter. The electrode may be provided for measuring the bio-signal in addition to the removal of the cardiac muscular tissue. Depending on a purpose of the treatment and a surgical procedure method, a treatment instrument such as a stent may be guided. The catheter body 63 is made of a highly biocompatible and flexible material to allow the electrode or other treatment instrument of a front end used in the ablation catheter or a mapping catheter to be guided to a target site.

Referring to FIG. 7, the light-wavelength analyzer 8 may include a processor 81, the display 83, an RF supply 85, a core connector 87 and a connector 89. The processor 81 may calculate the received light information. The display 83 may visually display the calculated shape of the catheter body 63 and the magnitude and direction of the force applied to the tip 61. The RF supply 85 may be connected to the catheter system 1 to supply Radio frequency (RF) thereto. The RF supply 85 may include the connector 89 and thus may be electrically connected to the catheter system 1 via the connector 89 and thus may easily supply the radio frequency thereto.

The coolant pump 9 may be connected to the catheter system 1 to supply coolant from the outside thereto. The catheter system 1 may have a channel defined therein for moving the coolant. The coolant supplied from the coolant pump 9 may flow inside the catheter system 1 and be delivered to the water supply holes 613.

Figure 8:
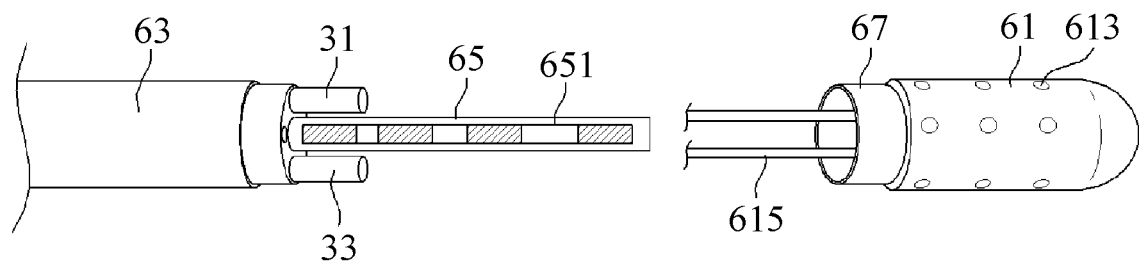
FIG. 8 shows an exploded view of a front end of a catheter according to an embodiment of the present disclosure.
Figure 9:
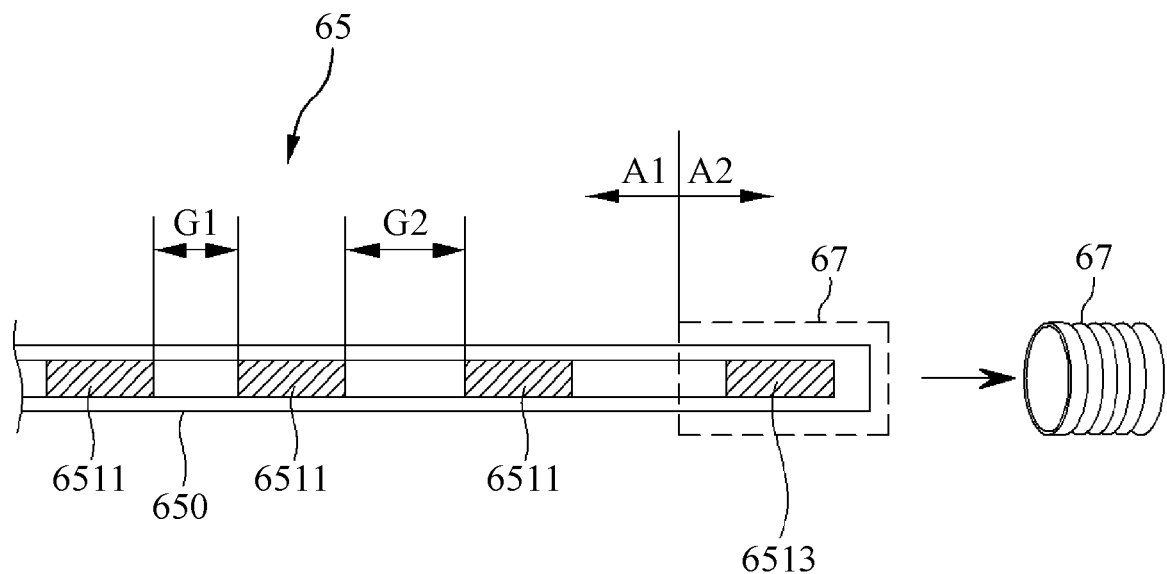
FIG. 9 shows an internal structure of an optical fiber of a catheter according to an embodiment of the present disclosure.

FIG. 8 shows an exploded view of a front end of the catheter 6 according to an embodiment of the present disclosure. FIG. 9 shows an internal structure of the optical fiber of the catheter according to one embodiment of the present disclosure.

Referring to FIG. 8 and FIG. 9, the catheter body 63 is divided into a first region A1 and a second region A2. The first region A1 may correspond to a path in which at least one channel is defined. The second region A2 may correspond to the front end having the tip 61 to which the external force is applied. Those regions are defined to clearly describe a structural feature and a function of the configuration. A path from the front end of the catheter 6 to the tip 61 and the elastic member 67 may correspond to the first region A1. A path of the front end for detecting the pressure of the tip 61 after the path of the first region A1 may correspond to the second region A2.

Figure 4A:
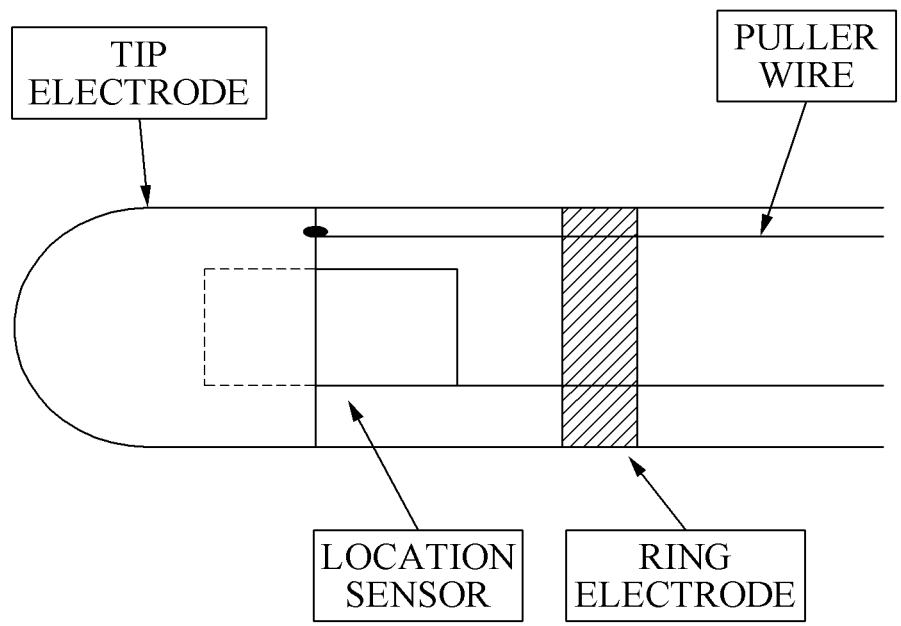
FIG. 4A and FIG. 4B show a conventional catheter system according to the magnetic field mapping technique.
Figure 4B:
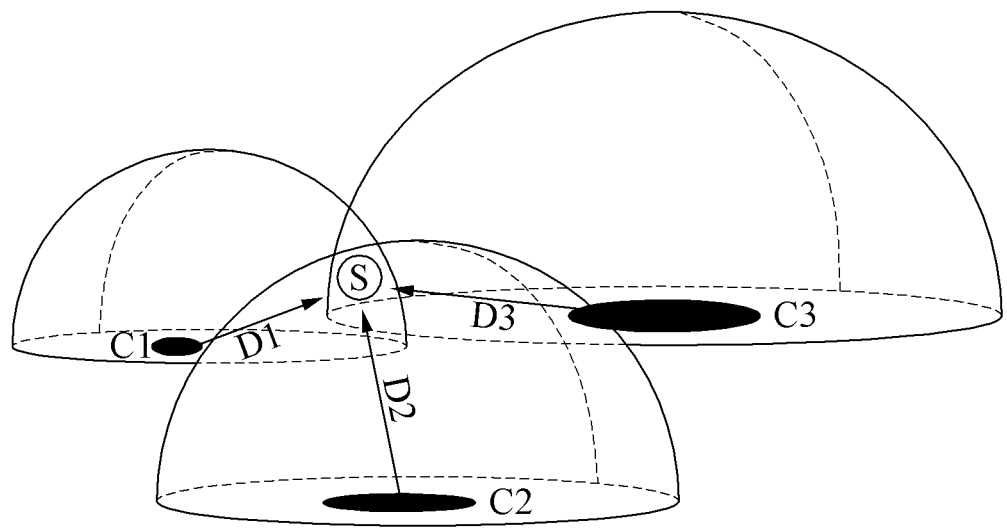
Figure 5:
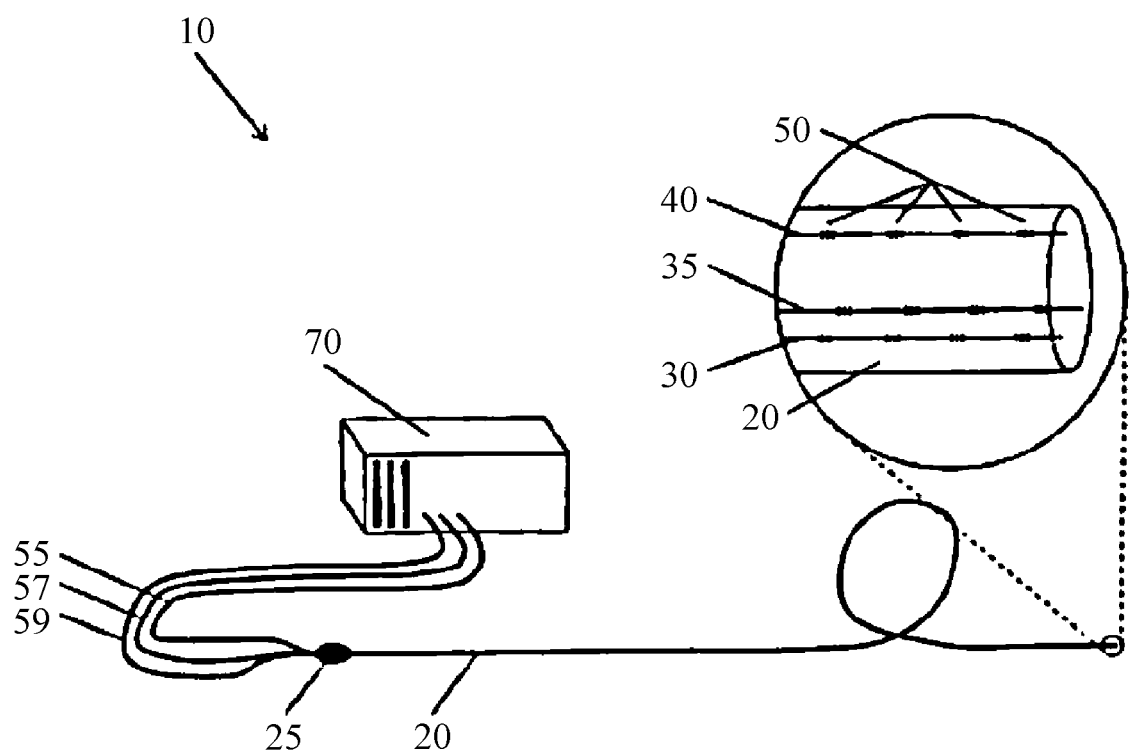
FIG. 5 shows a conventional optical fiber shape and position detection system.

One or more channels may be formed in the catheter body 63. Referring to FIG. 4A and FIG. 4B, it is shown that in an embodiment of the channels formed in the catheter body 63, a channel for receiving the optical fiber 65 for the pressure measurement, a channel for receiving the irrigation tube 31 for cooling the heated electrode, a channel for receiving the electrode wire 33 for supplying power to the electrode, and a channel for receiving the driving wire 615 for steering of the catheter 6 are formed.

The optical fiber 65 is received in the channel and has a plurality of FBGs 6511 and 6513 arranged along the longitudinal direction of the catheter body 63. The optical fiber 65 may be implemented such that a sheath 650 shields an optical core 651. A clad layer may be formed inside the sheath 650 to allow light to be delivered through the optical core 651 in a total reflection manner.

The optical fiber 65 may include a plurality of optical cores 651. An embodiment in which the plurality of optical cores 651 are present will be described later with reference to FIG. 10. Each optical core 651 has FBGs 6511 and 6513 as light grating sensors, and arranged in the longitudinal direction. The FBG refers to an optical device known as a fiber Bragg grating sensor and reflects light of wavelengths varying in response to changes in temperature or strain. The FBG is constructed by exposing short length photosensitive fibers to light of periodically distributed intensity using hologram disturbance or phase shift. When light in a wide range of wavelengths is transmitted to the FBG, reflection from each portion that replaces a refractive index are structurally disturbed only for a specific light wavelength as the Bragg wavelength. This causes the FBG to efficiently reflect light of a specific frequency, and causes a wavelength shift in the received light information. The FBGs are manufactured to have various Bragg wavelengths because the Bragg wavelength is a function of the grating spacing. Each of FBGs with various Bragg wavelengths reflects light of an unique wavelength in each wavelength band.

In the present embodiment, the FBGs 6511 and 6513 arranged in the longitudinal direction of the optical core 651 may sense that a specific point of the optical core 651 is bent to cause strain deformation. However, when the FBGs 6511 and 6513 are arranged in the optical core 651 at an equal spacing, and even though light having a broad wavelength is incident on the optical core 651, shifted wavelength information of the light as received may be partially lost due to the interference by gratings of the plurality of FBG 6511 and 6513. More specifically, a portion of the light incident on the optical core 651 hits a first located FBG and is reflected therefrom, and a remaining portion passes through the first located FBG. In the same way, a portion of the light that passes through the first FBG hits and is reflected from a second located FBG. The reflected light meets again with the first FBG, and a portion thereof passes through the first FBG and merges with the light reflected from the first FBG for the first time. A remaining portion thereof is reflected back from the first FBG and is directed to the second FBG. The same event happens repeatedly at gratings located after the second FBG. Light incident on the optical core 651 repeatedly reflects from and passing through the plurality of FBGs 6511 and 6513, thereby to cause interference with each other. As a result, even when the light of the broadband wavelength is incident, most of the shifted wavelength information is lost due to the multiple interferences. Thus, the sensitivity to distinguish the physical change such as the bending in each branching of the optical core 651 is insufficient.

Accordingly, in this embodiment, the plurality of FBGs 6511 and 6513 are arranged in the optical fiber 65 at different spacings. The plurality of FBGs 6511 and 6513 are arranged such that the spacing between adjacent FBGs may increase or decrease toward the front end. Referring to FIG. 9, a first spacing in a proximal portion is referred to as G1, while a second spacing at the front end as a distal portion is referred to as G2. The FBGs arranged in the front end direction are arranged such that the G2 is larger than the G1. That is, the spacing may gradually increase or decrease.

This arrangement allows the polarized reflective light to have different wavelengths when the light subjected to interference by multiple gratings exits through a light entrance back. More specifically, the polarized reflective light includes reflective light polarized in the longitudinal x-axis and reflective light polarized in the transverse y-axis, and the reflective light has different wavelength bands. Each independently represents the wavelength of the reflective light due to the plurality of gratings. As the spacing between the gratings varies, it is easy to detect the refractive state based on the detected wavelength change.

Further, the plurality of FBGs 6511 and 6513 senses the shape of the catheter body 63 based on the light wavelength information from the group of FBGs 6511 disposed in the first region A1, and may sense the external force applied to the tip 61 based on the light wavelength information from the group of FBGs 6513 arranged in the second region A2. A combination of the group of FBGs 6513 placed in the second region A2 and the group of FBGs 6511 placed in first region A1 may be used for shape sensing.

The light-wavelength analyzer 8 distinguishes between the shifted wavelength band of the first group of FBGs 6511 arranged in the first region A1 and the shifted wavelength band of the second group of FBGs 6513 arranged in the second region A2 to process the light information. In this connection, a plurality of grating sensors belonging to the first group of FBGs 6511 and the second group of FBGs 6513 are used to calculate the bending degree and direction at the corresponding position. A grating sensor belonging to the second group of FBGs 6513 is additionally used to calculate the contact force due to the axial pressurization or bending of the tip 61.

The elastic member 67 is provided to surround the optical fiber 65 inside the front end, and is made of a material having a different elastic force from that of the catheter body 63 to concentrate the external force applied to the tip 61 on the front end.

The elastic member 67 is located in the second region A2 and thus the group of FBGs 6513 arranged in the second region A2 is located in the elastic member 67.

The catheter 6 is most preferably implemented as a single piece of a single material so that there is no step. However, in order to accurately measure the magnitude and direction of the external force applied to the tip 61, it is required that a heterogeneous material with a different elastic force from that of the catheter body 63 is provided at the front end. In this embodiment, a significant measurement value may be obtained when the physical property change according to the pressure to the tip 61 is concentrated on the second group of FBGs 6513 located in the second region A2. If the catheter body 63 made of the same elastic material surrounds the second region A2, and even if an external force in the axial direction is applied to the front end tip 61, the magnitude of the external force is transmitted to most of the catheter body 63. Thus, the precise contact force of tip 61 may not be measured because the change of physical properties of the second region A2 is reflected into the change of physical properties of the first region A1 where the precise first group of FBGs 6511 is located. Further, even when the outward external force is applied to the front end tip 61, the change in the amount of light may be not precisely measured because the change in the physical properties is not concentrated on the second region A2 where the second group of FBGs 6513 is located. For this reason, it is desirable to provide the elastic member 67 made of a heterogeneous material and assembled to the front end of the catheter body 63 together with the tip 61 and surrounding the gap G located inside the catheter body 63. The elastic member 67 may be made of a more flexible material than the material of the catheter body 63. In an example, the elastic member 67 is embodied as an element such as a spring.

Figure 10:
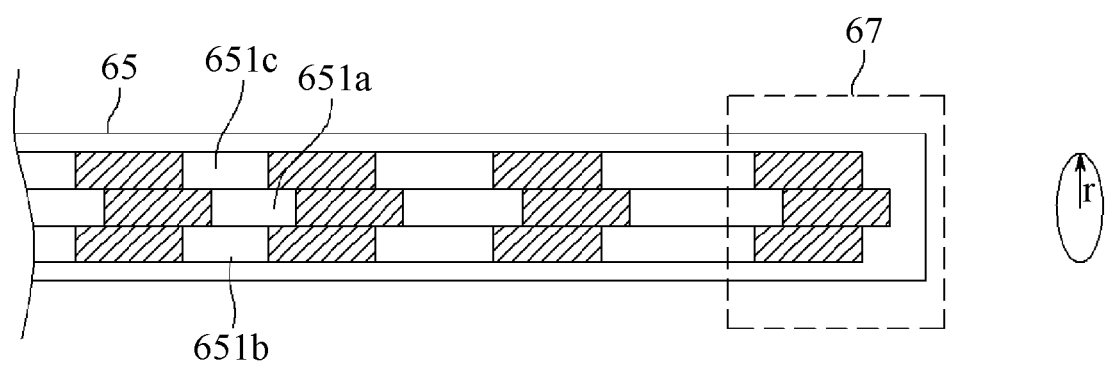
FIG. 10 shows an internal structure of an optical fiber according to another embodiment of the present disclosure.

FIG. 10 shows the internal structure of the optical fiber 65 composed of multiple optical cores 651a, 651b, and 651c according to another embodiment of the present disclosure.

Referring to FIG. 10, the optical fiber 65 has three or more optical cores 651a, 651b, and 651c. The three or more optical cores 651a, 651b, and 651c may be arranged around a linear axis of the catheter body 63 in a radius of 0.01 mm to 1.00 mm therefrom. More preferably, the spacing "r" may be within 0.2 mm. Referring to FIG. 9, in an embodiment, a configuration having the multiple optical cores 651a, 651b, and 651c in a single optical fiber 65 is disclosed. In another example, a configuration having three or more optical fibers 65 having a single optical core 651 in the catheter body 63 may be provided.

When at least three optical cores 651 are arranged for example at 120° spacing in the cross section of the optical fiber 65, triplet operation of light wavelength information received from the three optical cores 651 may be used to calculate the degree and direction of the bending of the optical cores 651. When each of the at least three optical cores 651 has a plurality of light gratings, three-dimensional deformation of the catheter body 63 may be calculated. A principle of the shape sensing using the three optical cores 651 may be referred to U.S. Pat. No. 7,781,724 by way of example. Referring to FIG. 5 to FIG. 8 and paragraph numbers [0046] to [0071] of U.S. Pat. No. 7,781,724, a method of calculating the direction and angle "a" of bending relative to the bending radius "r" as well as a x' axis as a center distance of a core boundary from a center of bending, using three strain values in three FBG optical cores located on the same cross section is disclosed. In the same principle, a bent shape of the catheter body 63 may be calculated by calculating a strain variable corresponding to shifted wavelength information, based on sensing information of at least three FBGs having different radii from the center of curvature.

Further, in the same principle, the three or more optical cores 651a, 651b, and 651c may sense the direction and magnitude of the external force exerted on the tip 61 based on three or more shifted wavelength information of light passing through the second group of FBGs 6513 placed in second region A2.

In one example, according to the present embodiment, the optical fiber 65 is introduced into a channel extending in the linear axis direction of the catheter body 63. In other words, the optical fiber 65 is placed in the center of the catheter body. The optical core 651 has a radius r within 0.20 mm.

The optical core 651 is less flexible than the catheter body 63 due to the nature of the material. Therefore, when the optical core 651 is located outwardly with respect to the linear axis of the catheter body 63, the bending range of the catheter 6 bent by the driving wire 615 may be limited. For this reason, it is preferable that as shown in FIG. 7, the optical fiber 65 is placed in the central channel corresponding to the linear axis of catheter body 63, while the irrigation tube 31 or the electrode wire 33 is disposed in the channel located outwardly with respect to the linear axis. This configuration is in contrast to U.S. Pat. No. 8,567,265, in which a plurality of optical cores should be disposed outside of the catheter body. This is a structural design that may improve the bending range of the catheter in consideration of the moving range of the inflexible optical fiber.

Referring back to FIG. 10, the three or more optical cores 651a, 651b, and 651c may distinguish between shifted wavelength information of light of different wavelength bands passing through the first group of FBGs 6511 disposed in the first region A1 respectively, and calculate the direction and angle of the bending of the optical fiber 65 using the distinguished light wavelength information to sense the shape of the catheter body 63.

In another embodiment, a path of incidence, reflection, and transmission of light to each of the three or more optical cores 651a, 651b, and 651c is completely separated from that of other optical cores. The light source, the light transmission path, and each of the wavelengths of light reflected from the FBGs are determined by a corresponding separate measuring sensor. The wavelength changes of light that occur as light passes through the group of FBGs 6511 in the first regions may be determined. The direction and angle of the bending of the optical fiber 65 may be calculated based on the discriminated three or more light information such that the shape of the catheter body 63 may be determined.

The three optical cores 651a, 651b, and 651c should be able to obtain reflective light in a discriminated manner from each other. For this reason, light of different wavelength bands may be incident on the three optical cores 651a, 651b, and 651c. In an example, light of R, G, and B wavelengths may be incident on three optical cores 651a, 651b, and 651c, respectively. The deformation of the shape generated in the first group of FBGs 6511 may be determined by comparing the light-amount of the red wavelength, the light-amount of the green wavelength, and the shift information of the blue wavelength.

In another embodiment, light of broadband wavelengths may be incident on the three or more optical cores 651a, 651b, and 651c at different timings respectively. In this case, the three or more optical cores 651a, 651b, and 651c may distinguish light information from each other based on the different timings when light having the same wavelength band passes through a group of FBGs 6511 arranged in the first region A1, respectively, and calculates the direction and angle of the bending of the optical fiber 65 using the distinguished light wavelength information to sense the shape of the catheter body 63.

Further, when light of the same wavelength band is incident on the three or more optical cores 651a, 651b, and 651c to form different light paths, the light information is discriminated from each other via the respective groups of FBGs 6511 disposed inside the optical cores 651a, 651b, and 651c of the first region A1, and the direction and angle of the bending of the optical fiber 65 may be calculated based on the discriminated light information such that the shape of the catheter body 63 may be determined.

The light-wavelength analyzer 8 may include the processor 81 and the display 83.

The light-wavelength analyzer 8 calculates the shape of the catheter body 63 using the light wavelength information of the group of FBGs 6511 disposed in the first region A1 among the plurality of FBGs and calculates the external force applied to the tip 61 using the light wavelength information of the group of FBGs 6513 disposed in the second region A2. The light-wavelength analyzer 8 may include a light source for injecting light of various wavelength bands or injecting light at different timings to discriminate between light wavelength information of the multiple optical cores 651a, 651b, and 651c. The processor 81 may calculate the received three light information. The display 83 may visually display the calculated shape of the catheter body 63 and the magnitude and direction of the force applied to the tip 61.

As described above, according to the present embodiment, the triplet calculation of three shifted wavelength information of light through the FBGs 6511 and 6513 provided in each of the three optical cores 651a, 651b, and 651c may allow detecting the location, direction and angle of the bending of the catheter body 63 to achieve the shape sensing of the catheter 6. Further, the optical fiber 65 is located in the center corresponding to the axis of the catheter body 63. In this connection, the three or more optical cores 651a, 651b, and 651c may be arranged around the linear axis in a radius of 0.01 mm to 1.00 mm from the linear axis. This may improve the bending range of the catheter in consideration of the moving range of the optical fiber lacking the flexibility.

Further, according to the present embodiment, the FBGs are arranged so that the spacing between adjacent FGBs arranged along the length direction of each of the optical cores 651a, 651b, and 651c increase or decrease in the front end direction. This minimizes the loss of the reflective light due to interference between the light passing through the FBGs to improve a resolution of detecting the bending position.

According to the present embodiment, the region in which the FBG is disposed in each of the optical cores 651a, 651b, and 651c is discriminated. The shifted wavelength corresponding to the group of FBGs 6511 in the first region is used for the shape sensing and pressure sensing. The shifted wavelength corresponding to the group of FBGs 6513 in the second region is used for the pressure sensing. Thus, the sensing assembly is configured to detect the shape and pressure of the catheter 6 using only three or more optical cores 651a, 651b, and 651c. Thus, the sensing assembly is particularly suitable as sensing means of a mapping catheter that must be implemented to have a small radius.

Although the present disclosure has been described in detail based on the representative embodiments above, those skilled in the art to which the present disclosure belongs will understand that various modifications may be made without departing from the scope of the present disclosure. Therefore, the scope of the present disclosure should not be limited to the embodiments as described but should be determined based on the claims to be described later and all changes or modifications derived from the claims and the equivalent concepts.

The invention claimed is:

1. A catheter comprising:
a catheter body having a first region and a second region, wherein a channel is formed in the first region, while the second region comprises a front end having a tip subjected to an external force;
an optical fiber inserted into the channel and having a plurality of Fiber Bragg Gratings (FBGs) arranged along a longitudinal direction of the catheter body; and
an elastic member to surround the optical fiber and disposed in the front end, wherein the elastic member is made of a material having a different elastic force from an elastic force of the catheter body to concentrate the external force applied to the tip on the front end, wherein the plurality of FBGs senses a shape of the catheter body based on light wavelength information corresponding to a first group of FBGs placed in the first region, and senses the external force applied to the tip based on light wavelength information of a second group of FBGs placed in the second region.

2. The catheter of claim 1, wherein the optical fiber has three or more optical cores, wherein the three or more optical cores are arranged around a linear axis of the catheter body in a radius of 0.01 mm to 1.00 mm from the axis.

3. The catheter of claim 1, wherein the plurality of FBGs are arranged in the optical fiber such that spacings between adjacent FBGs vary, wherein the spacings increase toward the front end.

4. The catheter of claim 1, wherein the plurality of FBGs are arranged in the optical fiber such that spacings between adjacent FBGs vary, wherein the spacings decrease toward the front end.

5. The catheter of claim 1, wherein the elastic member is disposed in the second region such that the second group of FBGs placed in the second region is located inside the elastic member.

6. The catheter of claim 1, wherein the optical fiber has three or more optical cores, wherein light of the same wavelength band is incident on the three or more optical cores.

7. The catheter of claim 1, wherein the optical fiber has three or more optical cores, wherein light of different wavelength bands are incident on the three or more optical cores.

8. The catheter of claim 7, wherein the three or more optical cores discriminate between shifted wavelength information of light of different wavelength bands passing through the first group of FBGs arranged in the first region, and calculate a direction and angle of the bending of the optical fiber based on the discriminated three or more light wavelength information to sense the shape of the catheter body.

9. The catheter of claim 1, wherein the optical fiber has three or more optical cores, wherein light is incident on the three or more optical cores at different timings.

10. The catheter of claim 9, wherein the three or more optical cores discriminate between light information based on the different timings at which the light of the same wavelength band passes through the first group of FBGs arranged in the first region, and calculate a direction and angle of the bending of the optical fiber based on the discriminated three or more light wavelength information to sense the shape of the catheter body.

11. The catheter of claim 9, wherein when light of the same wavelength band passes through the three or more optical cores in the first region to form different light paths, the three or more optical cores discriminate between the light information via the respective groups of FBGs disposed inside the optical cores, and calculate a direction and angle of the bending of the optical fiber based on the discriminated light wavelength information to sense the shape of the catheter body.

12. The catheter of claim 1, wherein the optical fiber has three or more optical cores, wherein the three or more optical cores sense a direction and a magnitude of the external force exerted on the tip based on shifted three or more wavelength information of light passing through the second group of FBGs placed in the second region.

13. The catheter of claim 1, wherein the plurality of FBGs are arranged in the optical fiber such that spacings between adjacent FBGs vary.

14. A catheter system comprising:
a catheter comprising:
a catheter body having a first region and a second region, wherein a channel is formed in the first region, while the second region comprises a front end having a tip subjected to an external force;
an optical fiber inserted into the channel and having a plurality of Fiber Bragg Gratings (FBGs) arranged along a longitudinal direction of the catheter body; and
an elastic member to surround the optical fiber and disposed inside in the front end, wherein the elastic member is made of a material having a different elastic force from an elastic force of the catheter body to concentrate the external force applied to the tip on the front end; and
a light-wavelength analyzer to calculate a shape of the catheter body based on light wavelength information corresponding to a first group of FBGs placed in the first region, and to calculate the external force applied to the tip based on light wavelength information of a second group of FBGs placed in the second region,
wherein the catheter comprises an electrode disposed outside of the catheter body to transmit an electrical signal to the light-wavelength analyzer through a wire placed inside the catheter body and to transmit energy to a tissue.

15. The catheter system of claim 14, wherein the optical fiber of the catheter has three or more optical cores,
wherein the light-wavelength analyzer calculates a direction and an angle of the bending of the optical fiber based on wavelength information of three or more light received from the three or more optical cores to sense the shape of the catheter body.

16. The catheter system of claim 14, wherein the plurality of FBGs are arranged in the optical fiber such that spacings between adjacent FBGs vary.

* * * * *